United States Patent [19]
Jones et al.

[11] Patent Number: 6,008,377
[45] Date of Patent: Dec. 28, 1999

[54] SYNTHESIS OF 3-[4-(2-AMINOETHOXY)-BENZOYL]-2-ARYL-6-HYDROXY-BENZO[B]THIOPHENES

[75] Inventors: Charles D Jones, Indianapolis; John M. McGill, Lafayette, both of Ind.

[73] Assignee: Eli Lilly and Company, Indianapolis, Ind.

[21] Appl. No.: 09/125,848

[22] PCT Filed: Mar. 20, 1996

[86] PCT No.: PCT/US96/03934

§ 371 Date: Aug. 21, 1998

§ 102(e) Date: Aug. 21, 1998

[87] PCT Pub. No.: WO97/34888

PCT Pub. Date: Sep. 25, 1997

Related U.S. Application Data

[60] Provisional application No. 60/013,674, Mar. 19, 1996.

[51] Int. Cl.$^6$ ..................... C07D 333/56; C07D 207/02; C07D 409/10; C07D 413/10
[52] U.S. Cl. ............................ 549/51; 549/57; 548/578; 546/202; 540/596; 544/146
[58] Field of Search ................. 549/51, 57; 548/578; 546/202; 540/596; 544/146

[56] References Cited

U.S. PATENT DOCUMENTS

| | | |
|---|---|---|
| 3,869,485 | 3/1975 | DeLong . |
| 4,007,204 | 2/1977 | Descamps et al. . |
| 4,133,814 | 1/1979 | Jones et al. . |
| 4,358,593 | 11/1982 | Jones et al. . |
| 4,380,635 | 4/1983 | Peters . |
| 4,418,068 | 11/1983 | Jones . |
| 5,169,860 | 12/1992 | Mohamadi et al. . |
| 5,470,854 | 11/1995 | von Angerer et al. . |
| 5,472,962 | 12/1995 | Koizumi et al. . |

FOREIGN PATENT DOCUMENTS

| | | |
|---|---|---|
| 2110062 | 12/1992 | Canada . |
| 0 062 503 | 10/1982 | European Pat. Off. . |
| 0 062 505 | 10/1982 | European Pat. Off. . |
| 0062 504 | 10/1982 | European Pat. Off. . |
| 0 605 193 A1 | 6/1994 | European Pat. Off. . |
| 0 635 264 A2 | 1/1995 | European Pat. Off. . |
| 2097 788 | 4/1982 | United Kingdom . |
| WO 93/10113 | 5/1993 | WIPO . |
| WO 95/10513 | 4/1995 | WIPO . |

OTHER PUBLICATIONS

Jones, et al., "Antiestrogens 2. Structure–Activity Studies in a Series of 3–Aroyl–2–arylbenzo [b]thiophene Derivatives Leading to [6–Hydroxy–[2–(4–hydroxyphenyl) benzo [b]thien–3–yl] [4–2–(1–piperidinyl) ethoxy]methanone Hydrochloride (LY156758), a Remarkably Effective Estrogen Antagonist with Only Minimal Instrinsic Estrogenicity," J. Med. Chem., 27, 1057–1066 (1984).

Pinney and Katzenellenbogen, Synthesis of a Tetrafluoro-–Substituted Aryl Azide and its Protio Analogue as Photoaffinity Labeling Reagents for the Estrogen Receptor, J. Org. Chem., 56, 3125–3133 (1991).

Cheronis, Semimicro Experimental Organic Chemistry, pp. 31–42 (J. de Graff Publish., 1958).

Wagner and Zook, Synthetic Organic Chemistry, pp. 171–172 (John Wiley & Sons, 1953).

Jackson, et al., "Cleavage of 12–alkylbenzo [a] phenothiazines with Lithium in Tetrahydrofuran: A Dealkylation–Desulphurization Reaction", J. Chem. Soc. (C.), pp. 1728–1729 (1969).

Kametani, et al., "A Novel Cleavage of Aryl Benzyl Ethers and Allyl Aryl Ethers by Sodium Bis (2–methoxyethoxy) aluminum Hydride. An Alternative Synthesis of Pentazocine", J. Org. Chem., 41(5 ), pp. 2545–2548 (1976).

Myerson and Toyokura, Crystallization as a Separations Process, Am. Chem. Society Symposium Series No. 438, 59 and 87, (1990).

Hanney, Treastise on Solid State Chemistry, vol. 3, Crystalline and Noncrystalline Solids, Plenum Press, pp. 89–90, (1977).

Zhu, et al., Synsthesis of bisflavone–type compounds (III). Selective demethoxylation of 1,4–bis (2',4',6'–trimethoxtphenyl–1, 4–butanedione CA 112: (1977).

Knight, "Its time to stop discriminating against PCT–USA National Phase Phatets", JPTOS Jun., pp. 386–400 (1997).

Fox, et al., "Physics and chem. Of the organic solid state" Interscience Pub. pp. 133–156 (1963).

Evans "An Introduction to Cyrstal Chemistry", Cambridge Press pp. 352–397 (1964).

*Primary Examiner*—Deborah C. Lambkin
*Attorney, Agent, or Firm*—Gilbert T. Voy

[57] ABSTRACT

The present invention is directed to chemical processes for preparing 2-aryl-6-hydroxy-3-[4-(2-aminoethoxyl)benzoyl] benzoyl]benzo[b]-thiophenes.

32 Claims, No Drawings

SYNTHESIS OF 3-[4-(2-AMINOETHOXY)-BENZOYL]-2-ARYL-6-HYDROXY-BENZO[B]THIOPHENES

Provisional application No. 60/013,674, Mar. 19, 1996 371 of of PCT/US/96/03934 Mar. 20, 1996.

BACKGROUND OF THE INVENTION

The present invention is directed to chemical processes for preparing 2-aryl-6-hydroxy-3-[4-(2-aminoethoxy)-benzoyl]benzo[b]thiophenes. The synthesis of aromatic ketones was reviewed by Gore in *Olah, Friedel-Crafts and Related Reactions*, Volume 3, Part 1, Chapter XXXI (1964). Generally, an acyl component and an aromatic substrate are reacted in the presence of a Lewis acid catalyst to produce the aromatic ketone. Suitable Lewis acid catalysts for this type of reaction include metal halides such as aluminum chloride, aluminum bromide, ferric chloride, and ferric bromide. See *Olah, Friedel-Crafts and Related Reactions*, Volume 1, Chapters II, III, and IV (1963).

The compounds prepared by the present processes were first described in U.S. Pat. No. 4,133,814. This patent described a number of processes for preparing the compounds, including the reaction of 2-arylbenzo[b]thiophenes-3-carboxylic acids with alkyl phenyl ethers. This patent taught the use of phenacyl, halophenacyl, End alkyl protecting groups for the phenolic hydroxyl groups. The alkyl protecting groups were removed by treating the phenolic ethers with pyridine hydrochloride. This patent also taught that the phenolic methyl ethers could be cleaved without affecting the 3-aroylalkoxy group by reacting with boron tribromide; however, the yield of the 3-aroylalkoxy-substituted compound was low.

The process described in U.S. Pat. No. 4,358,593 used particularly advantageous protecting groups for preparing 6-hydroxy-2-(4-hydroxyphenyl)-3-[4-(2-aminoethoxy)benzoyl]-benzo[b]thiophenes. These advantageous protecting groups are acetyl, substituted acetyl, benzoyl, alkylsulfonyl, and arylsulfonyl groups. This patent taught the use of classical Friedel-Crafts catalysts in the acylation of the protected 2-(4-hydroxyphenyl)-6-hydroxybenzo[b]thiophene, including metal halides such as aluminum chloride, aluminum bromide, zinc chloride, boron trifluoride, boron tribromilde, titanium tetrachloride, titanium tetrabromide, stannic chloride, stannic bromide, bismuth trichloride, and ferric chloride. Subsequent to acylation, the protecting group was generally removed under basic conditions.

A particularly useful compound from this series of 2-aryl-3-[4-(2-aminoethoxy)benzoyl]benzo[b]thiophenes is 6-hydroxy-2-(4-hydroxyphenyl)-3-[4-(2-piperidinoethoxy)-benzoyl]benzo[b]thiophene. This compound, as well as methods for its preparation, was first described in U.S. Pat. No. 4,418,068. This compound is a selective estrogen receptor modulator, useful for alleviating an estrogen-dependent pathological condition of an endocrine target organ. U.S. Pat. No. 5,393,763 described methods for the treatment of bone loss using this compound.

An improved process for the synthesis of 6-hydroxy-2-(4-hydroxyphenyl)-3-[4-(2-aminoethoxy)benzoyl]b was described in U.S. Pat. No. 4,380,635. These compounds were prepared by Friedel-Crafts acylation, using aluminum chloride as the catalyst, of a di-O-methyl-protected benzo[b]thiophene. The intermediate acylation product was demethylated by treating the acylation reaction mixture with a sulfur compound, such as methanethiol, ethanethiol, diethyl sulfide, and methionine. The product of this reaction generally contains aluminum salts and vario(us thioester by-products, which are difficult to remove from the benzothiophene. Also, the product has an unpleasant residual thiol or sulfide odor.

Boron halides, such as boron trichloride and boron tribromide, are useful for the cleavage of arylmethyl ethers. See Bahtt and Kulkarni, *Synthesis*, 249–282 (1983). Boron tribromide has previously been used to cleave arylmethyl ethers in benzothiophene compounds. See German Patent No. DE 4117512 A1.

The processes described above are not suitable for a large-scale synthetic process for preparing 2-aryl-6-hydroxy-3-[4-(2-aminoethoxy)benzoyl]benzo[b]thiophenes. A preferred process would use simple phenolic protecting groups, (such as methyl ethers), readily available starting materials, Friedel-Crafts acylation catalysts that are easily removed and do not present an environmental or health hazard upon disposal, a single reaction vessel, and provide the product in a form that is readily isolated. The process of the present invention fulfills all of these requirements.

SUMMARY OF THE INVENTION

The present invention is directed to efficient syntheses of 2-aryl-6-hydroxy-3-[4-(2-aminoethoxy)benzoyl]benzo[b]thiophenes which comprises acylating an aminoalkyl phenyl ether with a suitably-protected benzo[b]thiophene, and dealkylating the protected phenolic group(s) to provide the desired product. In accordance with the preferred aspect of the present invention, the acylation and dealkylation steps are performed successively in a single reaction vessel. More specifically, the present invention is directed to a process or preparing a crystalline solvate of a compound of the formula

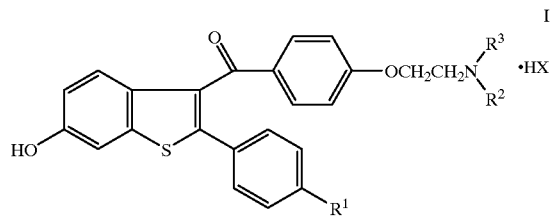

I wherein:
R$^1$ is hydrogen or hydroxyl;
R$^2$ and R$^3$ are independently C$_1$–C$_4$ alkyl, or R$^2$ and R$^3$ together with the adjacent nitrogen atom form a heterocyclic ring selected from the group consisting of pyrrolidino, piperidino, hexamethyleneimino, and morpholino; and
HX is HCl or HBr;
which comprises the steps of:
(a) acylating a compound of the formula

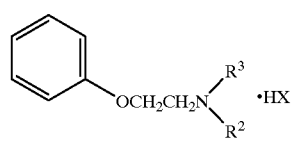

III wherein HX, R$^2$, and R$^3$ are as defined above, with an acylating agent of the formula

II

[structure: benzothiophene with R5O-, C(=O)R6 at 3-position, and 4-R4-phenyl at 2-position]

wherein:
   $R^4$ is hydrogen or $C_1$–$C_4$ alkoxy,
   $R^5$ is $C_1$–$C_4$ alkyl, and
   $R^6$ is chloro, bromo, or hydroxyl, in the presence of $BX'_3$, wherein X' is chloro or bromo;

(b) dealkylating one or more phenolic groups by reacting with additional $BX'_3$, wherein X' is as defined above; and (c) isolating the crystalline solvate.

A second aspect of the present invention is directed to a process for preparing a compound of the formula

IV

[structure: benzothiophene with R5O-, 3-benzoyl substituted with OCH2CH2N(R2)(R3), and 4-R4-phenyl at 2-position]

or the hydrochloride or hydrobromide salt thereof,
wherein:
   $R^4$ is hydrogen or $C_1$–$C_4$ alkoxy,
   $R^5$ is $C_1$–$C_4$ alkyl, and
   R2 and $R^3$ are independently $C_1$–$C_4$ alkyl, or $R^2$ and $R^3$ together with the adjacent nitrogen atom form a heterocyclic ring selected from the group consisting of pyrrolidino, piperidino,
   hexamethyleneimino, and morpholino;

which comprises acylating a compound of the formula

III

[structure: phenyl-OCH2CH2N(R2)(R3)·HX]

wherein:
   $R^2$ and $R^3$ are independently $C_1$–$C_4$ alkyl, or $R^2$ and $R^3$ together with the adjacent nitrogen atom form a heterocyclic ring selected from the group consisting of pyrrolidino, piperidino, hexamethyleneimino, and morpholino, and
   HX is HCl or HBr; with an acylating agent of the formula

II

[structure: benzothiophene with R5O-, C(=O)R6 at 3-position, and 4-R4-phenyl at 2-position]

wherein:
   $R^4$ is hydrogen or $C_1$–$C_4$ alkoxy,
   $R^5$ is $C_1$–$C_4$ alkyl, and
   $R^6$ is chloro, bromo, or hydroxyl;
An the presence of $BX'_3$, wherein X' is chloro or bromo.

DETAILED DESCRIPTION OF THE INVENTION

In the above formula, the term "$C_1$–$C_4$ alkyl" represents a straight alkyl chain having from 1 to 4 carbon atoms. Typical $C_1$–$C_4$ alkyl groups include methyl, ethyl, n-propyl, and n-butyl. The term "$C_1$–$C_4$ alkoxy" represents groups such as methoxy, ethoxy, n-propoxy, and n-butoxy. The preferred $C_1$–$C_4$ alkoxy group is methoxy.

The term "molar equivalents", as used herein, refers to the number of moles of the boron trihalide reagent in relation to the number of moles of the starting benzothiophene compound. For example, three millimoles of boron trichloride reacted with one millimole of the benzothiophene compound would represent three molar equivalents of boron trichloride.

The term "solvate" represents an aggregate that comprises one or more molecules of the solute, such as a formula I compound, with a molecule of solvent. Representative solvates are formed with methylene chloride, 1,2-dichloroethane, chloroform, and 1,2,3-trichloropropane.

The process of the present invention is useful for the synthesis of a series of compounds having antiestrogenic and antiandrogenic activity. See U.S. Pat. Nos. 4,418,068, 4,133,814, and 5,393,763. Representative Formula I compounds, the products of the processes of this inversion, include the following compounds: 6-hydroxy-2-phenyl-3-[4-(2-dimethylaminoethoxy)benzoyl]benzo[b]thiophene, 6-hydroxy-2-(4-hydroxyphenyl)-3-[4-(2-dimethylaminoethoxy)benzoyl]-benzo[b]thiophene, 6-hydroxy-2-phenyl-3-[4-(2-diethylaminoethoxy)benzoyl]benzo[b]thiophene, 6-hydroxy-2-(4-hydroxyphenyl)-3-[4-(2-diethylaminoethoxy)benzoyl]-benzo[b]thiophene, 6-hydroxy-2-phenyl-3-[4-(2-diisopropylaminoethoxy)benzoyl]benzo[b]thiophene, 6-hydroxy-2-(4-hydroxyphenyl)-3-[4-(2-diisopropylaminoethoxy)benzoyl]-benzo[b]thiophene, 6-hydroxy-2-phenyl-3-[4-(2-di-n-butylaminoethoxy)-benzoyl]benzo[b]thiophene, 6-hydroxy-2-(4-hydroxyphenyl)-3-[4-(2-di-n-butylaminoethoxy)benzoyl]-benzo[b]thiophene, 6-hydroxy-2-phenyl-3-[4-(2-pyrrolidinoethoxy)benzoyl]benzo[b]thiophene, 6-hydroxy-2-(4-hydroxyphenyl)-3-[4-(2-pyrrolidinoethoxy)benzoyl]-benzo[b]thiophene, 6-hydroxy-2-phenyl-3-[4-(2-piperidinoethoxy)benzoyl]benzo[b]thiophene, 6-hydroxy-2-(4-hydroxyphenyl)-3-[4-(2-piperidinoethoxy)benzoyl]-benzo[b]thiophene, 6-hydroxy-2-phenyl-3-[4-2-hexamethyleneiminoethoxy)benzoyl]benzo[b]thiophene, 6-hydroxy-2-(4-hydroxyphenyl)-3-[4-(2-hexamethyleneiminoethoxy)benzoyl]benzo[b]thiophene, 6-hydroxy-2-phenyl-3-[4-(2-morpholinoethoxy)benzoyl]benzo[b]- thiophene, 6-hydroxy-2-(4-hydroxyphenyl)-3-[4-(2-morpholinoethoxy)benzoyl]-benzo[b]-thiophene.

The preferred products of the claimed processes are the Formula I compounds wherein $R^1$ is hydroxyl, and $R^2$ and $R^3$ together with the adjacent nitrogen atom form a pyrrolidino, piperidino, or hexamethyleneimino group. Representative products from this preferred group include 6-hydroxy-2-(4-hydroxyphenyl)-3-[4-(2-pyrrolidinoethoxy)benzoyl]benzo[b]-thiophene, 6-hydroxy-2-(4-hydroxyphenyl)-3-[4-(2-piperldinoethoxy)benzoyl]benzo[b]thiophene, and 6-hydroxy-2-(4-hydroxyphenyl)-3-[4-(2-hexamethyleneiminoethoxy)benzoyl]henzo[b]-thiophene. More preferably, the products of the present invention are the Formula I compounds wherein $R^2$ and $R^3$ together with the adjacent nitrogen atom form a pyrrolidino or piperidino group. Representative products from this more preferred group include 6-hydroxy-2-(4-hydroxyphenyl)-3-[4-(2-pyrrolidinoethoxy)benzoyl]benzo[b]thiophene and 6-hydroxy-2-(4-hydroxyphenyl)-3-[4-(2-piperidinoethoxy)-benzoyl]benzo[b]thiophene. Most preferably, the product of the present invention is the Formula I compound wherein $R^1$ is hydroxyl, and $R^2$ and $R^3$ together with the adjacent nitrogen atom form a piperidino group. This most preferred product is 6-hydroxy-2-(4-hydroxyphenyl)-3-[4-(2-piperidinoethoxy)benzoyl]benzo[b]thiophene.

The present invention has several advantages over the prior art processes described above. The processes of the present invention use boron tribromide or boron trichloride as the acylation catalyst in place of aluminum chloride. Aluminum chloride is difficult to handle, especially on a commercial scale. Also, a large amount of aluminum chloride, typically six equivalents, is required for acylation and dealkylation. Aluminum chloride produces a large amount of aluminum by-products, which are insoluble in the work-up solvents and difficult to remove from the pharmaceutically active 2-aryl-6-hydroxy-3-[4-(2-aminoethoxy)benzoyl]-benzo[b]thiophenes. The aluminum chloride-catalyzed reactions are generally a heterogeneous mixture. The processes of the present invention are homogeneous, and the boron by-products are soluble in the work-up solvents. Further, the aluminum chloride-catalyzed dealkylation required the addition of a mercaptan or a sulfide for cleavage of the alkyl aryl ethers producing dialkyl sulfides, which exhibit offensive odors. These mercaptans or sulfides are removable by recrystallization; however, this produces a recrystallization solvent with the odorous impurities. The processes of the present invention eliminate the use of aluminum and the use of odorous mercaptans and sulfides.

Typically, the art processes produced a high quantity of related substances and high levels of residual aluminum salts in the final product. Representative related substances include 6-hydroxy-2-(4-methoxyphenyl)-3-[4-2-piperidinoethoxy)benzoyl]benzo[b]-thiophene, 2-(4-hydroxyphenyl)-6-methoxy-3-[4-(2-piperidinoethoxy)-benzoyl]benzo[b]thiophene, 6-hydroxy-3-(4-hydroxybenzoyl)-2-(4-hydroxyphenyl)benzo[b]thiophene, propyl 4-(2-piperidinoethoxy)thiobenzoate, methyl 4-(2-piperidinoethoxy)-benzoate, 6-hydroxy-2-(4-hydroxyphenyl)-3-[4-(2-piperidinoethoxy)benzoyl]-5-[4-(2-piperidinoethoxy)benzoyl]benzo[b]-thiophene, and 6-hydroxy-2-(4-hydroxyphenyl)-3-[4-(2-piperidinoethoxy) benzoyl]-7-[4-(2-piperidinethoxy)-benzoyl]benzo[b]thiophene. In the process of the present invention, the boron by-products are easily removed from the final product. Also, the present process avoids the disposal of aluminum waste. When the reaction is carried out in 1,2-dichloroethane, the reactions are homogeneous allowing the use of higher concentrations, and produce crystalline solvates that are readily isolated.

The Formula II and III compounds, the starting materials for the present invention, are prepared using standard synthetic organic methods. The Formula II starting compound can be readily obtained by a synthesis which is exemplified below and outlined in Scheme I.

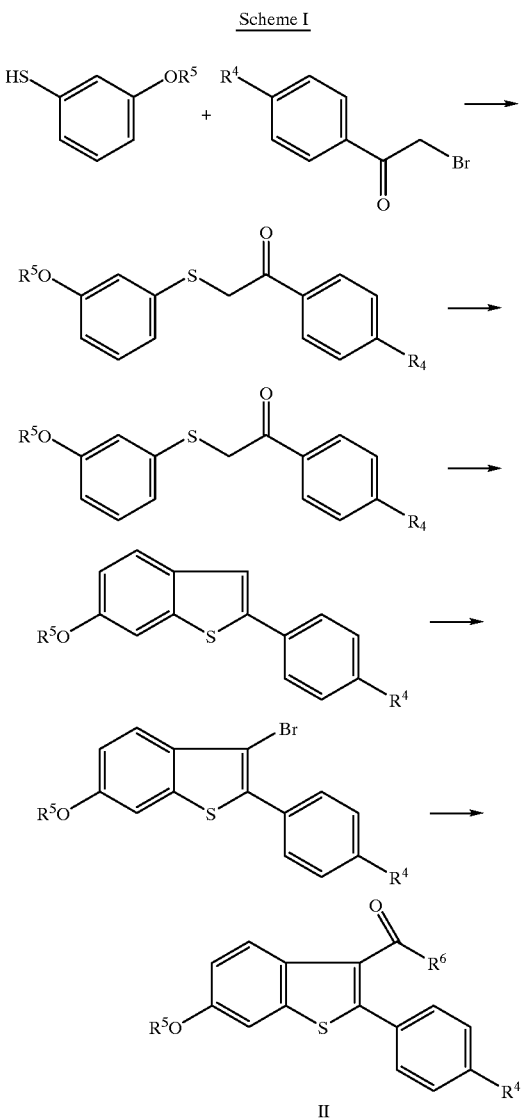

Scheme I

The Formula II compounds, wherein $R^4$, $R^5$, and $R^6$ are as defined above, can be prepared by first reacting a 3-alkoxybenzenethiol with a phenacyl or 4'-alkoxyphenacyl bromide in the presence of a strong base. Suitable bases for this transformation include, but are not limited to, potassium hydroxide and sodium hydroxide. The reaction is typically carried out in ethanol or a mixture of water and ethanol at a temperature of about 0° C. to about 50° C.

The next step is cyclization of the arylphenacylsulfide. The cyclization is conveniently carried out by heating the arylphenacylsulfide in polyphosphoric acid. The cyclization is typically carried out at a temperature of about 80° C. to about 120° C., preferably between 85° C. and 90° C. The intermediate benzothiophene is typically purified by recrystallization. For example, when $R^4$ is methoxy and $R^5$ is methyl, the intermediate benzothiophene compound may be recrystallized from ethyl acetate.

The intermediate benzothiophene compound is converted to a Formula II compound by a sequence of steps comprising halogenation, lithiation, and carboxylation. First, the benzothiophene intermediate is converted to the corresponding 3-bromo analog by reaction with bromine in a halogenated hydrocarbon solvent. Suitable halogenated solvents for this reaction include carbon tetrachloride, chloroform, and methylene chloride; preferably a mixture of carbon tetrachloride and chloroform. This transformation is carried out at a temperature of about 25° C. to about 55° C. The intermediate 3-bromo benzothiophene compound is isolated using standard techniques, such as by recrystallization.

The 3-bromo intermediate is lithiated aind carboxylated to prepare the Formula II. The 3-bromo benzothiophene compound is reacted with an alkyl lithium, such as n-butyl lithium in a dry, polar organic solvent to produce the lithiated compound. Suitable solvents for this reaction include anhydrous diethyl ether, anhydrous tetrahydrofuran, and anhydrous dimethoxyethane. This reaction is typically run at the temperature of about −78° C. to about −50° C. The intermediate 3-lithiated benzothiophene compound is treated with carbon dioxide, either solid or gaseous, to produce the Formula II compound wherein $R^6$ is OH. This transformation is conveniently carried out in the same solvent as the lithiation reaction. The acid is typically isolated by acidification of the reaction mixture followed by recrystallization. For example, when $R^4$ is methoxy, $R^5$ is methyl, and $R^6$ is hydroxy, the Formula II compound can be recrystalized from absolute ethanol. The Formula II compounds, wherein $R^6$ is chloro or bromo, are prepared by halogenating the Formula II compounds wherein $R^6$ is hydroxyl. Suitable halogenating agents include oxalyl chloride, thionyl chloride, thionyl bromide, phosphorous tribromide, triphosgene, and phosgene. Preferably, $R^6$ is chloro. Suitable solvents for this reaction include methylene chloride, 1,2-dichlorobenzene, chlorobenzene, and 1,2-dichloroethane. Preferably, the halogenation reaction is carried out in the same solvent as the subsequent acylation reaction. A catalytic amount of dimethylformamide, from about 0.05 to about 0.25 equivalents, is added to the chlorination reaction. When the reaction is carried out in 1,2-dichloroethane, the reaction is complete after about two to five hours at about 47° C. Preferably, the chlorination reaction and acylation reaction are carried out successively in the same reaction vessel.

The aminoalkyl phenyl ether for the present process, a Formula III compound, can be prepared as shown in Scheme II, wherein the variables $R^2$, $R^3$, and HX are as defined above.

Scheme II

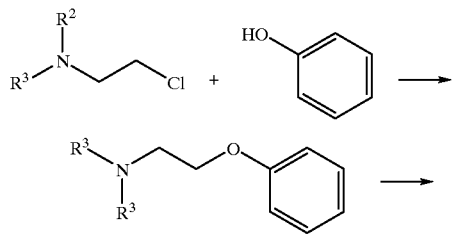

-continued

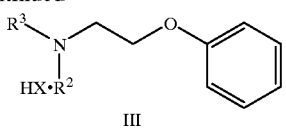

III

Generally, a phenol is alkylated with a chioroethylamine in the presence of an inorganic base and isolated as the hydchloride or hydrobromide salt to produce the Formula III compounds. Examples of chloroethylamines that are useful for preparing the Formula I compounds are 1-(2-chloroethyl)piperidine, 4-(2-chloroethyl)morpholine, and 1-(2-chloroethyl)pyrrolidine. Suitable inorganic bases for this alkylation include potassium carbonate and sodium carbonate. Suitable solvents for this alkylation are non-reactive polar organic solvents such as imethyl ethyl ketone and dimethylformamide.

The 2-aryl-6-hydroxy-3-[4-(2-aminoethoxy)benzoyl[b]-thiophenes can be prepared by acylation and subsequent dealkylatlon of the phenolic groups in two distinct steps, or sequentially in a "one-pot" reaction. The step-wise synthesis is described in the following paragraphs. The acylated benzothiophene intermediate, a Formula IV compound, is prepared as shown in Scheme III, wherein $R^2$, $R^3$, $R^4$, $R^5$, $R^6$, and HX are as defined above.

Scheme III

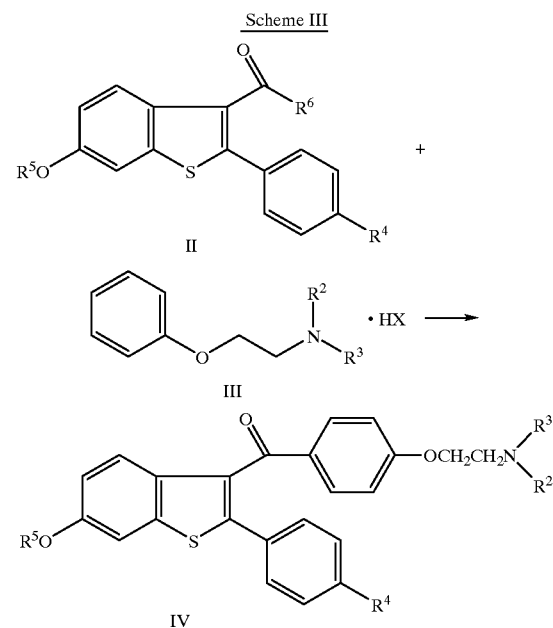

Generally, benzothiophene intermediate II is reacted with a Formula II compound, using boron trichloride or boron tribromide as the acylation catalyst. The ree.ction is carried out in an organic solvent, such as chlorobenzene, methylene chloride, 1,2-dichloroethane, 1,2-dichlorobenzene, bromobenzene, chloroform, 1,1,2,2-tetrachloroethane, 1,2,3-trichloropropane, and fluorobenzene. Preferably, the acylation is carried out in methylene chloride, chlorobenzene, or 1,2-dichloroethane. Most preferably, the acylation step is carried out in methylene chloride. Because boron tribromide is more preferred for dealkylation of phenolic ethers, the preferred boron trihalide for catalyzing acylation is boron trichloride. For boron trichloridecatalyzed reactions in methylene chloride, the acylation reaction can be performed at room temperature, with minimal dealkylation of the Formula III and IV compounds. In other solvents, the acylation reaction is carried out at lower temperatures, such as −10° C. to 10° C., to minimize the amount of dealkylation of the reaction starting material and product. When $R^6$ is chloro, at least 2 molar equivalents of the boron trihalide reagent are required for acylation. When the 3-benzoic acid is used as an acylating agent ($R^6$=OH), five equivalents of the boron trihalide are typically used. The Formula IV compound may be isolated as the hydrochloride or hydrobromide salt, or as the free base.

In the step-wise process, the acylated intermediate (Formula IV compound) is dealkylated to produce the Formula compound as shown in Scheme IV, wherein $R^1$, $R^2$, $R^3$, $R^4$, $R^5$, and HX are as defined above.

Scheme IV

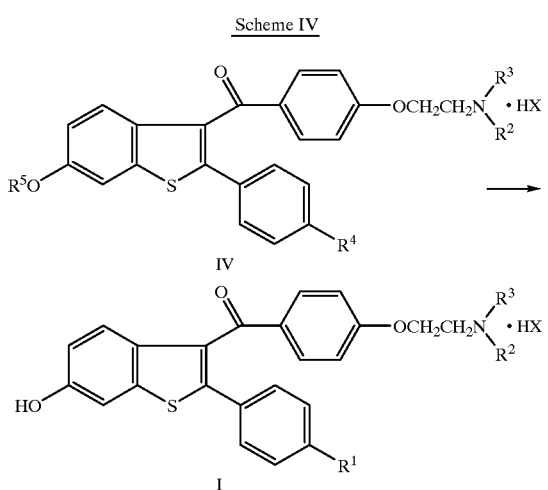

The Formula I compound can be produced by reacting the hydrochloride or hydrobromide salt of the Formula IV compound with boron tribromide or boron trichloride. The preferred boron trihalide for dealkylation is boron tribromide. This dealkylation reaction can be carried out in a variety of organic solvents, such as methylene chloride, chlorobenzene, 1,3-dichloroethane, chloroform, 1,1,2,2-tetrachloroethane, 1,2,3-trichloropropane, 1,2-dichlorobenzene, and fluorobenzene. The preferred solvent is 1,2-dichloroethane. When the acid addition salt is used as a starting material, the amount of by-product resulting from dealkylation of the aiminoethyl group is minimized. When methylene chloride is used as the solvent and the boron reagent is boron trichloride, the reaction is generally carried out at a temperature of about 55° C. to about 75° C., producing the Formula I compound with no detectable cleavage of the aminoethyl group. In other solvents, such as chloroform, 1,2-dichloroethane, chlorobenzene, 1,2-dichlorobenzene, and fluorobenzene, the dealkylation occurs readily at ambient temperatures. For example, when 1,2-dichloroethane is the solvent, the reaction is generally carried out at 25° C. to 35° C. with no detectable cleavage of the aminoethyl group. At least four equivalents of the boron trihalide reagent are typically used for complete reaction within a reasonable time.

Preferably, the Formula I compounds are prepared by a "one-pot" synthesis from the Formula II and III compounds as shown in Scheme V, wherein $R^1$, $R^2$, $R^3$, $R^4$, $R^5$, $R^6$, and HX are as defined above.

Scheme V

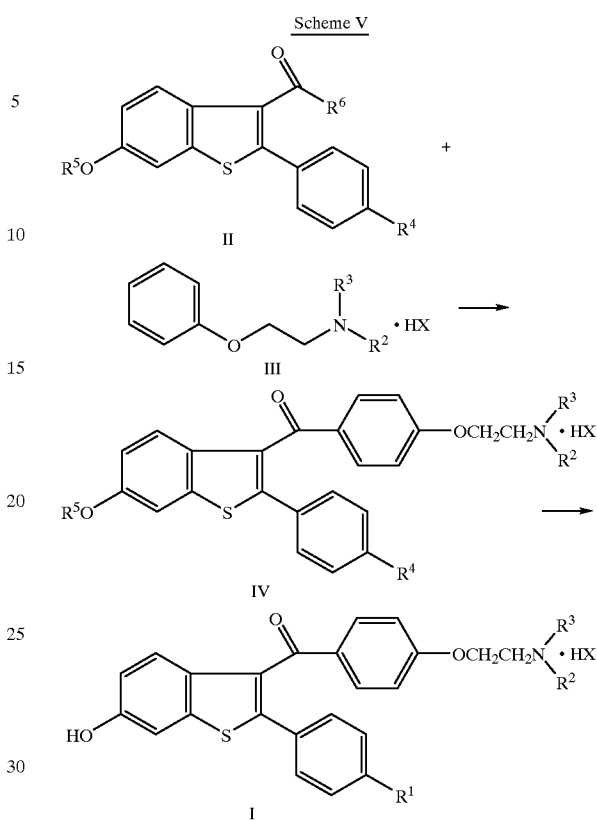

The benzothiophene Formula II compound is reacted with the Formula III compound in the presence of boron trichloride or boron tribromide; boron trichloride is preferred for the "one-pot" process. The reaction can be carried out in a variety of organic solvents, such as chloroform, methylene chloride, 1,2-dichloroethane, 1,2,3-trichloropropane, 1,1,2,2-tetrachloroethane, 1,2-dichlorobenzene, chlorobenzene, and fluorobenzene. The preferred solvent for this synthesis is 1,2-dichloroethane. The reaction is carried out at a temperature of about −10° C. to about 25° C., preferably at 0° C. The reaction is best carried out at a concentration of the benzothiophene Formula II compound of about 0.2 M to about 1.0 M. Preferably, two to five molar equivalent of boron trichloride are added to the reaction mixture, most preferably three molar equivalents. The acylation reaction is generally complete after about two hours to about eight hours.

The acylated benzothiophene, the Formula IV compound, is converted to a Formula I compound without isolation. This conversion is performed by adding additional boron trihalide and heating the reaction mixture. Preferably, two to five molar equivalents of boron tricrloride are added to the reaction mixture for dealkylation, most preferably three molar equivalents. This reaction is carried out at a temperature of about 25° C. to about 40° C., preferably at 35° C. The reaction is generally complete after about 4 to 48 hours.

The acylation/dealkylation reaction is quenched with an alcohol or a mixture of alcohols. Suitable alcohols for use in quenching the reaction include methanol, ethanol, and isopropanol. Preferably, the acylation/dealkylation reaction mixture is added to a 95:5 mixture of ethanol and methanol (3A ethanol). The 3A ethanol can be at root temperature or heated to reflux, preferably at reflux. When the quench is performed in this manner, the Formula I compound conveniently crystallizes from the resulting alcoholic mixture. Generally, 1.25–3.75 mL of alcohol per millimole of the benzothiophene starting material are used.

The crystalline product of this "one-pot" process, when $BCl_3$, is used, is isolated as the solvate of he hydrochloride salt. These crystalline solvates are obtained under a variety of conditions. The preparation of a solivate of the Formula I compound, wherein $R^1$ is hydroxyl, HX is HCl, and $R^2$ and $R^3$ together with the adjacent nitrogen atom form a piperidino group, was described previously. Jones et a., *J. Med. Chem.*, 27, 1057 (1984). Generally, the form of the product of the present process is determined by choice of acylation/dealkylation solvent, boron trihalide, and work-up conditions.

A particularly useful solvate of the formula I compound is the 1,2-dichloroethane solvate. This solvate is prepared by carrying out the "one-pot" acylation/dealkylation process in 1,2-dichloroethane. When $R^1$ is hydroxyl, $R^2$ and $R^3$ together with the adjacent nitrogen form a piperidino group, and HX is HCl, the 1,2-dichloroethane solvate can exist in two distinct forms. One crystalline solvate form, termed crystal form I, is prepared by quenching the boron trichloride-catalyzed acylation/dealkylation reaction with ethanol. Preferably, a mixture of ethanol and methanol (95:5) is used in the preparation of this crystal form.

A second crystalline solvated form is termed crystal form II. This particular form is prepared by the boron trichloride-catalyzed acylation/dealkylation process using methylene chloride or chloroform as the solvent.

The following examples further illustrate the processes of the present invention. The examples are not intended to be limiting to the scope of the invention in any respect, and should not be so construed. All experiment, were run under a positive pressure of dry nitrogen. All solvents and reagents were used as obtained. The percentages are generally calculated on a weight (w/w) basis; except for HPLC solvents which are calculated on a volume (v/v) basis. Proton nuclear magnetic resonance ($^1$H NMR) spectra were obtained on a Bruker AC-300 FTNMR spectrometer at 300.135 MHz. Melting points were measured on a Mel-Temp II apparatus (Laboratory Devices, USA), and are reported uncorrected.

The reactions were generally monitored for completion using high performance liquid chromatography (HPLC) or thin-layer chromatography (TLC). The acylation, dealkylation, or acylation/dealkylation reactions were monitored for completion using high performance liquid chromatography (HPLC). A sample of the reaction mixture was assayed using a Zorbax RX-C8 column (25 cm×4.6 mm ID, 5 µparticle), eluting with a gradient as shown below:

| GRADIENT SOLVENT SYSTEM | | |
|---|---|---|
| Time (min.) | A (%) | B (%) |
| 0 | 70 | 30 |
| 12 | 70 | 30 |
| 14 | 25 | 75 |
| 16 | 70 | 30 |
| 25 | 70 | 30 |

A: 0.075 phosphate (pH = 2.0)
B: acetonitrile

The reaction mixture was analyzed by diluting a 0.1 mL to 0.2 mL sample to 50 mL with a 60:40 mixture of A/B.

PREPARATION 1

6-Methoxy-2-(4-methoxyphenyl)benzo[b]thiophene

A solution of 3-methoxybenzenethiol (100 grams) and potassium hydroxide (39.1 grams) in water (300 mL) was added to denatured ethanol (750 mL), and the resulting mixture cooled to about 0° C. The cold mixture was treated with 4'-methoxyphenacyl bromide (164 grams) in several small portions. Upon complete addition, the mixture was cooled for an additional ten minutes, then allowed to warm to room temperature. After three hours, the mixture was concentrated in vacuo, and the residue treated with water (200 mL). The resulting mixture was treated with ethyl acetate, and the phases were separated. The organic phase was washed with water (2x), sodium bicarbonate solution (2x), and sodium chloride solution (2x). The organic phase was then dried over magnesium sulfate, filtered, and evaporated to dryness in vacuo to give 202 grams of α-(3-methoxyphenylthio)-4-methoxyacetophenone. This crude product was crystallized from methanol and washed with hexane to give 158 grams. Melting point 53° C.

Polyphosphoric acid (930 grams) was heated to 85° C. and treated with the intermediate product from above (124 grams) in small portions over 30 minutes. Upon complete addition, the resulting mixture was stirred at 90° C. After an additional 45 minutes, the reaction mixture was allowed to cool to room temperature. This mixture was treated with crushed ice while the mixture was cooled in an ice bath. The resulting mixture was treated with water (100 mL) producing a light pink precipitate. The precipitate was isolated by filtration, washed with water and methanol, and dried in vacuo at 40° C. to give 119 grams of 6-methoxy-2-(4-methoxyphenyl)benzo[b]thiophene. This crude product was slurried in hot methanol, filtered, and washed with cold methanol. The resulting solid material was recrystallized from ethyl acetate (4 liters), filtered, washed with hexane, and dried in vacuo to 68 grams of the title compound. Melting point 187–190.5° C.

PREPARATION 2

3-bromo-6-methoxy-2-(4-methoxyphenyl)benzo[b]thiophene

A mixture of the compound prepared as described in Preparation 1 (10.0 g) and chloroform (400 mL) was heated on a steambath. Upon complete dissolution, the chloroform solution was treated with a solution of bromine (5.9 g) in carbon tetrachloride as the chloroform solution cooled from 50° C. to 25° C. After an additional half hour at room temperature, the solution was concentrated ini vacuo to give an oil which crystallized upon standing. This crystalline material was dissolved in hot absolute ethanol (600 mL), and the volume of the resulting ethanol solution concentrated to about 400 mL by distillation. Small white needles appeared which were collected by filtration and dried in vacuo, to give 11.9 g of the total compound.

Analysis calculated for $C_{16}H_{13}BrO_2S$: C, 55.03; H, 3.75; Br, 22.88. Found: C, 55.30; H, 3.52; Br, 23.00.

PREPARATION 3

6-Methoxy-2-(4-methoxyphenyl)benzo[b]-thiophene-3-carboxcyclic Acid

A solution of n-butyl lithium in hexane (85 mL, 1.6 M solution) was added to anhydrous diethyl ether (400 mL), and the resulting solution cooled to about −78° C. The compound prepared as described in Preparation 2 (40 g) was dissolved in (150 mL), and the resulting solution was slowly added to the cold n-butyl lithium over a period of 1½ hr. After an additional half hour, an additional portion of n-butyl lithium (25 mL) as added. After an additional half hour, the dry ice/acetone cooling bath was removed, and carbon dioxide was bubbled through the solution as it slowly warmed to room temperature. After standing overnight, the resulting mixture was poured onto ice (2 L) and acidified with 1 N hydrochloric acid. The resulting white precipitate was collected by filtration, washed with water, and air dried. This material was added to hot, 1 N sodium hydroxide (150 mL) and the resulting solution was filtered. The filtrate was slowly acidified with concentrated hydrochloric acid. The resulting white precipitate was collected by filtration, washed with water, and air dried. This material was crystallized from absolute ethanol to give 2.715 g of the title compound as small white prisms. The proton nuclear magnetic resonance ($^1$H NMR) spectrum was consistent with the structure or the title compound.

PREPARATION 4

6-Methoxy-2-(4-methoxyphenyl)benzo[b]-thiophene-3-carboxyclic Acid Chloride

A solution of the compound prepared as described in Preparation 3 (300 mg) and dimethylformamide (2 drops) in 1,2-dichloroethane (5 mL) was cooled to about 0° C. This cold solution was treated with oxalyl chloride (110 μL) over a five-minute period. After stirring overnight at room temperature, the reaction solution was evaporated to dryness in vacuo. The residue was dissolved in 1,2-dichloroethane (2×10 mL), and the resulting solution evaporated to dryness. This material was used in the acylation reaction without further purification.

PREPARATION 5

Phenyl 2-Piperidinoethyl Ether Hydrochloride

A mixture of phenol (46.5 g), 1-(2-chloroethyl) piperidine (103.5 g), and potassium carbonate (207 g) in dimethylformamide (900 mL) was heated to reflux. After refluxing for two hours, the reaction mixture was allowed to cool to room temperature. This mixture was filtered, and the solids washed with dimethylformamide (100 mL). The combined filtrates was concentrated in vacuo to a brown oil. This oil was dissolved with ethyl acetate (400 mL), and the resulting solution was washed with water (2×200 mL) and saturated brine (2×200 mL). The ethyl acetate solution was dried over magnesium sulfate, filtered, and concentrated in vacuc to a brown oil. This oil was dissolved in methanol (100 mL), and the resulting solution acidified with 3% methanolic hydrochloric acid (prepared from acetyl chloride and methanol, 500 mL). The resulting solution was evaporated to dryness in vacuo. The residue (74 g) was crystallized from 1-propanol (800 mL) and ethyl acetate (500 mL) to give 59.6 g of the title compound as an off-white crystalline solid. Melting point 179–180° C.

EXAMPLE 1

6-Hydroxy-2-(4-hydroxyphenyl)-3-[4-(2-piperidinoethoxy)-benzoyl]benzo[b]thiophene Hydrochloride 1,2-Dichloroethane Solvate A solution of the acid chloride prepared as described in Preparation 4 (302 mg) in 1,2-dichloroethane (4 mL) is treated with the compound prepared as described in Preparation 5 (320 g). The resulting solution was cooled to about 0° C. and treated with boron trichloride (1.2 mL, 2.35 M solution). The 2.35 M solution of boron trichloride in 1,2-dichloroethane is prepared by condensing boron trichloride (2 mL) in a cold graduated cylinder (dry ice/acetone bath) and adding 1,2-dichloroethane at 0° C. to a total volume of 10 mL. The reaction mixture was stirred at 0° C. After six hours, an additional quantity of boron trichloride (1.2 mL, 2.35 M solution) was added to the reaction mixture. The reaction mixture is warmed to 35° C. for about 16–20 hours. The resulting reaction mixture was cooled to about 18° C. and treated with ethanol (5 mL), allowing the resulting solution to reflux. The resulting solution was seeded with a crystal of the title compound, stirred at room temperature for about 65 hours, and filtered. The filter cake was washed with cold methanol (1×5 mL), and the desired compound dried in vacuo at 40° C., to give 220 mg of the title compound. Melting point 250–265° C.

$^1$HNMR (d$_6$-DMSO): δ 10.55 (br s, 1H), 9.82 (s, 1h), 9.8 (s, 1H), 7.68 (d, 2H), 7.33 (d, 1H), 7.26 (d, 1H), 7.14 (d, 2H), 6.93 (d, 2H), 6.85 (dd, 1H), 6,68 (d, 2H), 4.43 (m, 2H), 3.93 (s, 1.5H, 1,2-dichlorethane solvate), 3.45 (m, 2H), 3.41 (m, 2H), 2.95 (m, 2H), 1.77 (m, 4H), 1.68 (m, 1H), 1.36 (m, 1H).

PREPARATION 6

6-Hydroxy-2-(4-hydroxyphenyl)-3-[4-(2-piperidinoethoxy)-benzoyl]benzo[b]thiophene Hydrochloride A solution of sodium hydroxide (0.313 g) in methanol (10 mL) was diluted with additional methanol (40 mL) and water (10 mL). This solution was treated with the compound prepared as described in Example 1 (4.0 g). The methanolic phase was treated with 2 N hydrochloric acid (4 mL), producing a crystalline slurry. After one hour, the crystalline produce was filtered, washed with methanol (5 mL), and dried at 60° in vacuo to give 2.23 g of the title compound.

We claim:

1. A process for preparing a crystalline solvate of a compound of the formula

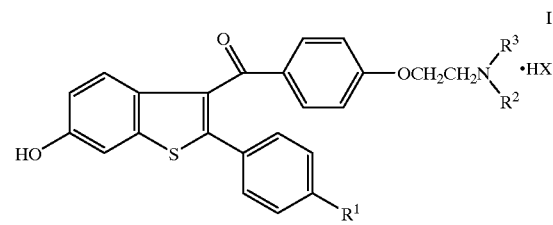

wherein:

R$^1$ is hydrogen or hydroxyl;

R$^2$ and R$^3$ are independently C$_1$–C$_4$ alkyl, or R$^2$ and R$^3$ together with the adjacent nitrogen atom form a heterocyclic ring selected from the group consisting of pyrrolidino, piperidino, hexamethyleneimino, and morpholino; and HX is HCl or HBr;

which comprises the steps of:

(a) acylating a compound of the formula

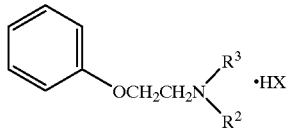

wherein: HX, $R^2$, and $R^3$ are as defined above, with an acylating agent of the formula

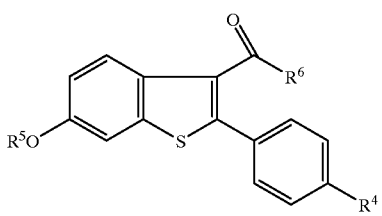

wherein:
$R^4$ is hydrogen or $C_1$–$C_4$ alkoxy;
$R^5$ is $C_1$–$C_4$ alkyl; and
$R^6$ is chloro, bromo, or hydroxyl;
in the presence of $BX'_3$, wherein X' is chloro or bromo;
(b) dealkylating one or more phenolic groups of the acylation product of step (a) by reacting with additional $BX_3'$, wherein X' is as defined above; and
(c) isolating the crystalline solvate.

2. The process of claim 1 wherein $R^6$ is chloro and HX is HCl.

3. The process of claim 2 wherein $R^1$ is hydroxyl and $R^4$ is $C_1$–$C_4$ alkoxy.

4. The process of claim 3 wherein $R^2$ and $R^3$ together with the adjacent nitrogen atom form a heterocyclic ring selected from the group consisting of pyrrolidino, piperidino, and hexamethyleneimino.

5. The process of claim 4 wherein X' is chloro.

6. The process of claim 5 wherein $R^4$ is methoxy and $R^5$ is methyl.

7. The process of claim 6 wherein $R^2$ and $R^3$ together with the adjacent nitrogen atom form a piperidino group.

8. The process of claim 7 wherein the acylation is conducted in the presence of 2–5 molar equivalents of $BCl_3$.

9. The process of claim 7 wherein the dealkylation is conducted in presence of 3–10 molar equivalents of $BCl_3$.

10. The process of claim 7 wherein the reaction solvent is one or more solvents selected from the group consisting of chloroform, methylene chloride, 1,2-dichloroethane, 1,2,3-trichloropropane, 1,1,2,2-tetrachloroethane, 1,2-dichlorobenzene, chlorobenzene, and fluorobenzene.

11. The process of claim 7 wherein the reaction solvent is 1,2-dichloroethane.

12. A process for preparing a compound of the formula

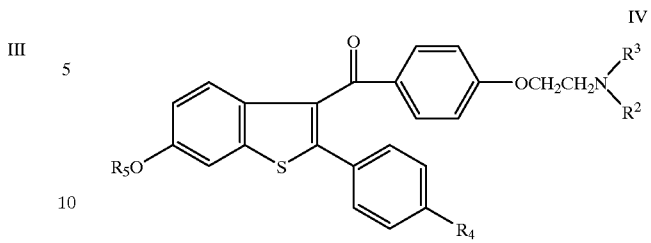

or the hydrochloride or hydrobromide salt thereof, wherein:
$R^4$ is hydrogen or $C_1$–$C_4$ alkoxy;
$R^5$ is $C_1$–$C_4$ alkyl; and
$R^2$ and $R^3$ are independently $C_1$–C4 alkyl, or $R^2$ and $R^3$ together with the adjacent nitrogen atom form a heterocyclic ring selected from the group consisting of pyrrolidino, piperidino, hexamethyleneimino, and morpholino;
which comprises acylating a compound of the formula

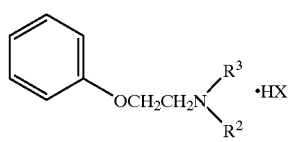

wherein:
$R^2$ and $R^3$ are independently $C_1$–$C_4$ alkyl, or $R^2$ and $R^3$ together with the adjacent nitrogen atom form a heterocyclic ring selected from the group consisting of pyrrolidino, piperidino, hexamethyleneimino, and morpholino; and
HX is HCl or HBr;
with an acylating agent of the formula

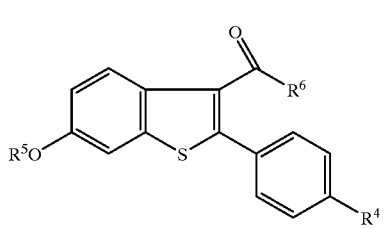

wherein:
$R^4$ and $R^5$ are as defined above, and
$R^6$ is chloro, bromo, or hydroxyl; in the presence of $BX'_3$, wherein X' is chloro or bromo.

13. The process of claim 12 wherein $R^6$ is chloro and HX is HCl.

14. The process of claim 13 wherein $R^4$ is $C_1$–$C_4$ alkoxy.

15. The process of claim 14 wherein $R^2$ and $R^3$ together with the adjacent nitrogen atom form a heterocyclic ring selected from the group consisting of pyrrolidino, piperidino, and hexamethyleneimino.

16. The process of claim 15 wherein X' is chloro.

17. The process of claim 16 wherein $R^4$ is methoxy, and $R^5$ is methyl.

18. The process of claim 17 wherein $R^2$ and $R^3$ together with the adjacent nitrogen atom form a piperidino group.

19. The process of claim 18 wherein the acylation is conducted in the presence of 2–5 molar equivalents of $BCl_3$.

20. The process of claim 18 wherein the reaction solvent is one or more solvents selected from the group consisting of chloroform, methylene chloride, chlorobenzene, 1,2-dichloro-ethane, 1,2,3-trichloropropane, 1,1,2,2-tetrachloroethane, 1,2-dichlorobenzene, bromobenzene, and fluorobenzene.

21. The process of claim 18 wherein the reaction solvent is methylene chloride.

22. The process of claim 21 wherein $R^7$ is methyl.

23. A process for preparing a crystalline solvate of a compound of the formula

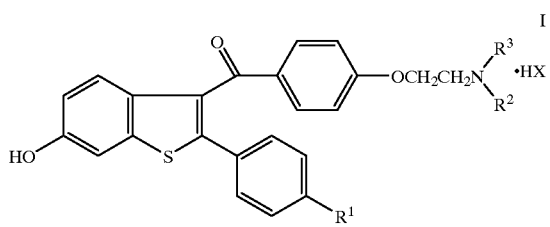

I wherein:
$R^1$ is hydrogen or hydroxyl;
$R^2$ and $R^3$ are independently $C_1$–$C_4$ alkyl, or $R^2$ and $R^3$ together with the adjacent nitrogen atom form a heterocyclic ring selected from the group consisting of pyrrolidino, piperidino, hexamethyleneimino, and morpholino; and
HX is HCl or HBr;
which comprises the steps of:
(a) chlorinating with phosgene, oxallyl chloride, or thionyl chloride a compound of the formula

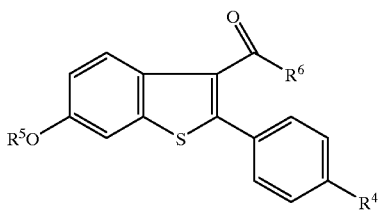

II wherein:
$R^4$ is hydrogen or $C_1$–$C_4$ alkoxy, and
$R^5$ is $C_1$–$C_4$ alkyl, and
$R^6$ is hydroxyl,
to produce a formula II compound wherein $R^6$ is chloro;
(b) acylating a compound of the formula

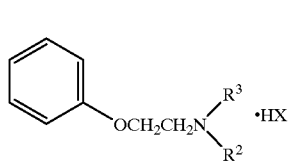

III wherein:
HX, $R^2$, and $R^3$ are as defined above, with a compound of formula II, wherein $R^6$ is chloro, in the presence of $BX'_3$, wherein X' is chloro or bromo;

(c) dealkylating one or more phenolic groups of the acylation product of step (b) by reacting with additional $BX'_3$, wherein X' is as defined above; and
(d) isolating the crystalline solvate.

24. The process of claim 23 wherein $R^1$ is hydroxyl and $R^4$ is $C_1$–$C_4$ alkoxy.

25. The process of claim 24 wherein X' is chloro and HX is HCl.

26. The process of claim 25 wherein $R^4$ is methoxy and $R^5$ is methyl.

27. The process of claim 26 wherein $R^2$ and $R^3$ together with the adjacent nitrogen atom form a piperidino group.

28. A process for preparing a crystalline solvate of a compound of the formula

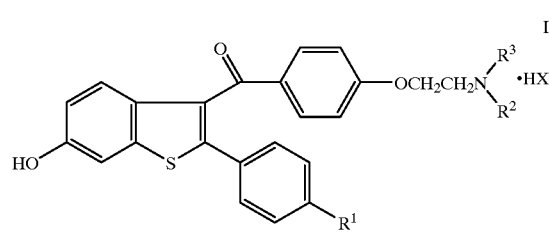

I wherein:
$R^1$ is hydrogen or hydroxyl;
$R^2$ and $R^3$ are independently $C_1$–$C_4$ ailkyl, or $R^2$ and $R^3$ together with the adjacent nitrogen atom form a heterocyclic ring selected from the group consisting of pyrrolidino, piperidino, hexamethyleneimino, and morpholino; and
HX is HCl or HBr;
which comprises the steps of:
(a) chlorinating a compound of the formula

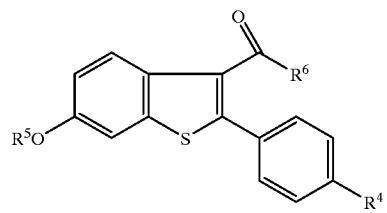

II wherein:
$R^4$ is hydrogen or $C_1$–$C_4$ alkoxy, and
$R^5$ is $C_1$–$C_4$ alkyl, and
$R^6$ is hydroxyl,
to produce a formula II compound wherein $R^6$ is chloro;
(b) acylating a compound of the formula

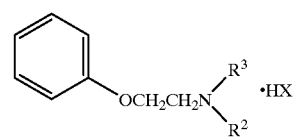

III wherein:
HX, $R^2$, and $R^3$ are as defined above, with a compound of formula II, wherein $R^6$ is chloro, in the presence of $BX'_3$, wherein X' is chloro or bromo;
(d) dealkylating one or more phenolic groups of the acylation product of step (c) by reacting with additional $BX'_3$, wherein X' is as defined above; and
(e) isolating the crystalline solvate.

29. The process of claim 28 wherein $R^1$ is hydroxyl and $R^4$ is $C_1$–$C_4$ alkoxy.

30. The process of claim 29 wherein X' is chloro and HX is HCl.

31. The process of claim 30 wherein $R^4$ is methoxy and $R^5$ is methyl.

32. The process of claim 31 wherein $R^2$ and $R^3$ together with the adjacent nitrogen atom form a piperidino group.

* * * * *